United States Patent
Georgakopoulos et al.

(10) Patent No.: US 8,401,652 B2
(45) Date of Patent: Mar. 19, 2013

(54) DEVICES AND METHODS FOR TREATMENT OF HEART FAILURE AND ASSOCIATED CONDITIONS

(75) Inventors: Dimitrios Georgakopoulos, Maple Grove, MN (US); Eric Grant Lovett, Mendota, MN (US)

(73) Assignee: CVRx, Inc., Minneapolis, MN (US)

(*) Notice: Subject to any disclaimer, the term of this patent is extended or adjusted under 35 U.S.C. 154(b) by 0 days.

(21) Appl. No.: 13/360,339

(22) Filed: Jan. 27, 2012

(65) Prior Publication Data

US 2012/0123506 A1    May 17, 2012

Related U.S. Application Data

(62) Division of application No. 12/485,895, filed on Jun. 16, 2009.

(60) Provisional application No. 61/061,938, filed on Jun. 16, 2008.

(51) Int. Cl.
*A61N 1/36* (2006.01)

(52) U.S. Cl. .......................................... 607/44

(58) Field of Classification Search .............. 607/44, 607/2
See application file for complete search history.

(56) References Cited

U.S. PATENT DOCUMENTS

| | | | |
|---|---|---|---|
| 5,707,400 A | 1/1998 | Terry, Jr. et al. | |
| 5,800,468 A | 9/1998 | Holmstrom | |
| 6,115,633 A | 9/2000 | Lang et al. | |
| 6,522,926 B1 | 2/2003 | Kieval et al. | |
| 6,985,774 B2 | 1/2006 | Kieval et al. | |
| 7,580,746 B2 | 8/2009 | Gilkerson et al. | |
| 7,643,875 B2 | 1/2010 | Hell, Jr. | |
| 7,873,413 B2 | 1/2011 | McCabe et al. | |
| 8,116,873 B2 | 2/2012 | Anderson et al. | |
| 2002/0058877 A1 | 5/2002 | Baumann et al. | |
| 2002/0151816 A1 | 10/2002 | Rich et al. | |
| 2003/0149450 A1 | 8/2003 | Mayberg | |
| 2004/0102712 A1 | 5/2004 | Belaleazar et al. | |
| 2004/0220632 A1 | 11/2004 | Burnes | |
| 2005/0154418 A1 | 7/2005 | Kieval et al. | |
| 2005/0251033 A1 | 11/2005 | Scarantino et al. | |

(Continued)

FOREIGN PATENT DOCUMENTS

| WO | WO 2004/075928 A2 | 9/2004 |
|---|---|---|
| WO | WO 2006/031902 A2 | 3/2006 |

(Continued)

OTHER PUBLICATIONS

International Search Report and Written Opinion; PCT/US2012/020516; Jun. 25, 2012; 12 pages.

(Continued)

*Primary Examiner* — Carl H Layno
*Assistant Examiner* — Paula J Stice
(74) *Attorney, Agent, or Firm* — Patterson Thuente Christensen Pedersen, P.A.

(57) ABSTRACT

Devices and methods of use are described for detecting and treating an undesirable level of fluid in a pulmonary circulation of a patient. An exemplary system may include an implantable baroreflex activation device including an electrode configured to be implanted proximate a baroreptor within a patient, an implantable sensor configured to provide an indication of a fluid level within the patient, and a control system coupled to the baroreflex activation device and the sensor. The control system may be programmed to automatically detect a level of a fluid in a pulmonary circulation of the patient with the sensor and upon detecting an undesirable level of the fluid in the pulmonary circulation, delivering a therapy via the electrode of the baroreflex activation device to reduce the level of fluid in the pulmonary circulation.

12 Claims, 14 Drawing Sheets

U.S. PATENT DOCUMENTS

| | | |
|---|---|---|
| 2005/0251212 A1 | 11/2005 | Kieval et al. |
| 2006/0004417 A1 | 1/2006 | Rossing et al. |
| 2006/0047218 A1 | 3/2006 | Bloom et al. |
| 2006/0074453 A1 | 4/2006 | Kieval et al. |
| 2006/0282145 A1 | 12/2006 | Caparso et al. |
| 2006/0293712 A1 | 12/2006 | Kieval et al. |
| 2007/0156061 A1 | 7/2007 | Hess |
| 2009/0036777 A1 | 2/2009 | Zhang et al. |
| 2009/0132002 A1 | 5/2009 | Kieval |
| 2009/0143837 A1 | 6/2009 | Rossing et al. |
| 2009/0198302 A1 | 8/2009 | Anderson et al. |
| 2010/0004714 A1 | 1/2010 | Georgakopoulos et al. |
| 2012/0095523 A1 | 4/2012 | Yared |

FOREIGN PATENT DOCUMENTS

| | | |
|---|---|---|
| WO | WO 2007/136851 | 11/2007 |

OTHER PUBLICATIONS

U.S. Appl. No. 12/485,895, filed Jun. 16, 2009, Dimitrios Georgakopoulos et al.

U.S. Appl. No. 12/986,077, filed Jan. 6, 2011, Nadim Yarden.

Fig. 6

| | | |
|---|---|---|
| EJECTION DURATION | $ED(\text{msec}) = T_i - T_f$ | |
| HEART RATE | $HR(\text{BEATS/MIN}) = 60/T_T$ | |
| PRESSURE AT FIRST SHOULDER | $P_1(\text{mm Hg}) = P[T_1]$ | |
| PRESSURE AT SECOND SHOULDER | $P_2(\text{mm Hg}) = P[T_2]$ | |
| PRESSURE AT DIASTOLE | $P_d(\text{mm Hg}) = P[T_f]$ | |
| PRESSURE AT SYSTOLE | $P_3(\text{mm Hg}) = P[T_p]$ | |
| PRESSURE AT END-SYSTOLE | $P_{ES}(\text{mm Hg}) = P[T_i]$ | |
| AUGMENTED PRESSURE | $AP(\text{mm Hg}) = P_2 - P_1$ | |
| MEAN DIASTOLIC PRESSURE | $MDP(\text{mm Hg}) = \dfrac{\sum_{i=T_i}^{T_T} P_i}{T_T - T_i}$ | |
| MEAN ARTERIAL PRESSURE | $MAP(\text{mm Hg}) = \dfrac{\sum_{i=T_f}^{T_T} P_i}{T_T}$ | |
| MEAN SYSTOLIC PRESSURE | $MSP(\text{mm Hg}) = \dfrac{\sum_{i=T_f}^{T_f} P_i}{T_i - T_f}$ | |
| AUGMENTATION INDEX | $AI(\%) = 100 \times \dfrac{P_2 - P_d}{P_1 - P_d}$ | |
| TENSION TIME INDEX | $TTI(\text{mm Hg} \cdot \text{BEATS/MIN}) = HR \times MSP \times (T_i - T_f)$ | |
| DIASTOLIC TIME INDEX | $DTI(\text{mm Hg} \cdot \text{BEATS/MIN}) = HR \times MDP \times (T_T - T_i)$ | |

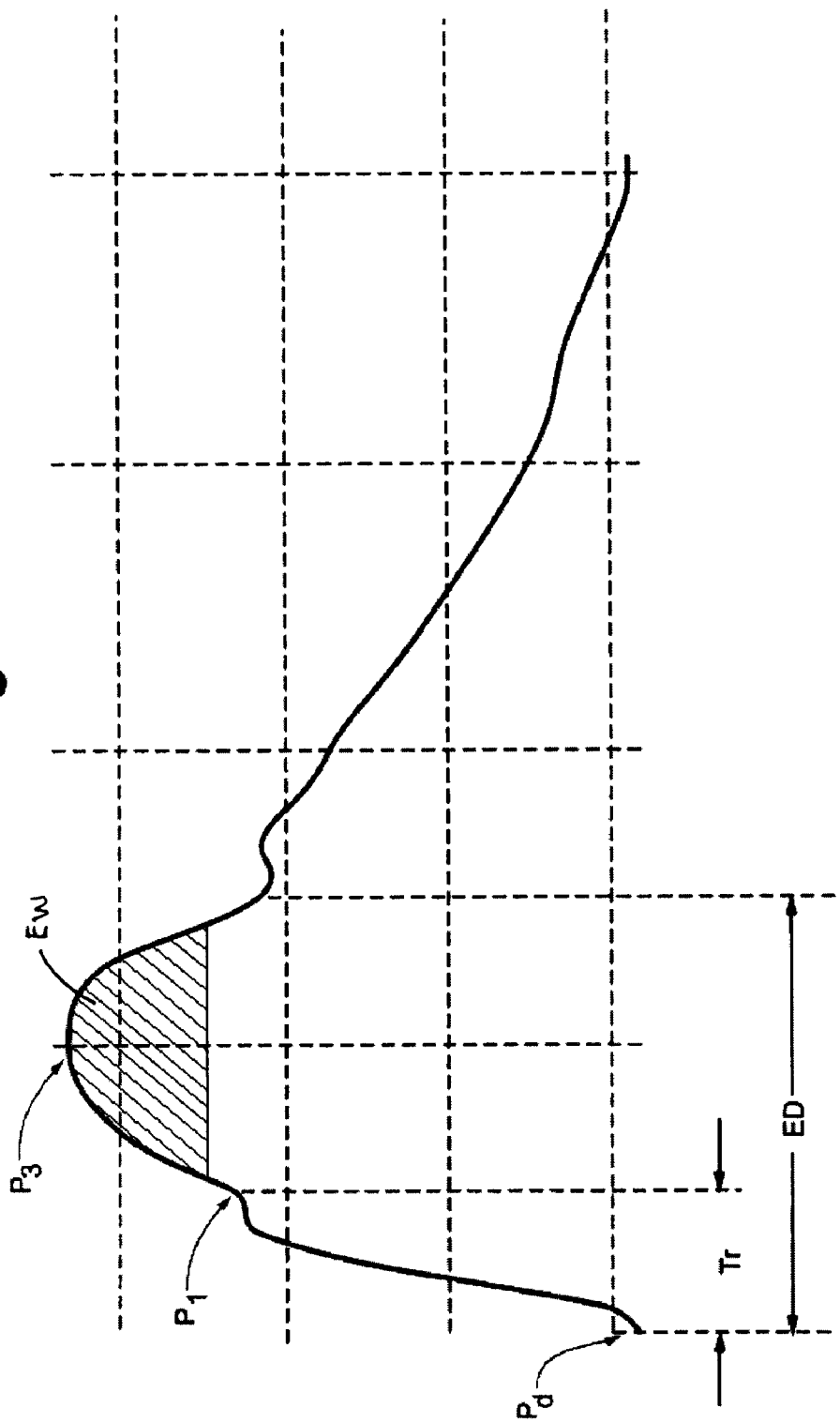

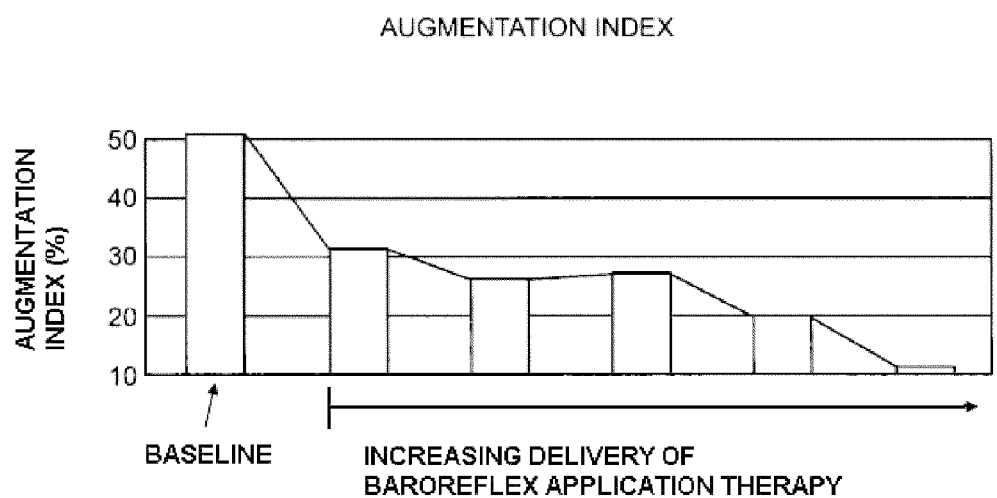

Fig. 8A

| N = 19 | BASELINE | Δ 3 MONTHS | Δ 12 MONTHS |
|---|---|---|---|
| OFFICE CUFF SYSTOLIC BP (mmHg) | 179.4 ± 24.2 | -22.8 ± 25.8‡ | -27.0 ± 24.7‡ |
| OFFICE CUFF DIASTOLIC BP (mmHg) | 106.0 ± 17.6 | -12.3 ± 18.7* | -13.2 ± 19.9* |
| HEART RATE (bpm) | 72.9 ± 11.4 | -4.6 ± 10.1 | -2.6 ± 8.6 |
| SEPTAL WALL THICKNESS (mm) | 14.0 ± 3.2 | -1.0 ± 1.2‡ | -1.7 ± 1.9‡ |
| LV POSTERIOR WALL THICKNESS (mm) | 13.4 ± 2.4 | -0.8 ± 0.9‡ | -1.5 ± 1.1‡ |
| LV MASS (g) | 288 ± 80.7 | -33.8 ± 30.8‡ | -55.8 ± 43.7‡ |
| LV MASS INDEX (g/m$^2$) | 132.4 ± 32.4 | -15.5 ± 13.3‡ | -26.0 ± 18.2‡ |
| RELATIVE WALL THICKNESS | 0.54 ± 0.12 | -0.02 ± 0.05 | -0.05 ± 0.06† |
| ANTIHYPERTENSIVE MEDICATIONS (#) | 5.2 ± 1.9 | -0.3 ± 1.8 | -0.5 ± 0.8* |

Fig. 8B

| CHANGE IN CARDIAC STRUCTURE, BP, HEART RATE AND MEDICATION | BASELINE (N=32) | Δ 3 MONTHS (N=32) | Δ 12 MONTHS (N=19) |
|---|---|---|---|
| LVOT DIAMETER (mm) | 19.59±1.92 | +0.59±1.13* | +0.74±1.05* |
| LVMI (g/m2) | 138.8±36.0 | -17.9±16.3‡ | -26.0±18.2‡ |
| PULSE PRESSURE (mmHg) | 74.9±16.2 | -11.4±18.1‡ | -14.3±12.3‡ |
| SYSTOLIC BP (mmHg) | 179.8±24.9 | -22.8±30.5‡ | -27.8±25.1‡ |
| DIASTOLIC BP (mmHg) | 105.0±17.4 | -11.4±19.7† | -13.5±20.4* |
| HEART RATE (bpm) | 72.5±10.5 | -4.9±9.0† | -3.2±8.3 |
| ANTI-HTN MEDICATIONS (#) | 5.2±1.7 | -0.3±1.5 | -0.5±0.8* |

VALUES: MEAN±SD *p≤0.01 †p<0.005 ‡p≤0.001

*Fig. 8C*

|  N=21  | BASELINE | Δ 4 MONTHS | Δ 13 MONTHS |
|---|---|---|---|
| ARTERIAL COMPLIANCE (mL/mmHg) | 1.12 ± 0.40 | 0.16 ± 0.34 | 0.21 ± 0.37 |
| EJECTION FRACTION | 64.6 ± 5.1 | 1.9 ± 2.6 | 1.9 ± 6.8 |
| IVS THICKNESS AT END DIASTOLE | 14.0 ± 3.1 | -1.0 ± 1.1 | -1.6 ± 1.9 |
| eMVO2 (mmHg*BPM) | 12788 ± 2617 | -1958 ± 2771 | -2210 ± 2635 |
| eMVO2/60 | 213.1 ± 43.6 | -32.6 ± 46.2 | -36.8 ± 43.9 |

|  | BASELINE | BAT |
|---|---|---|
| HR | 72 | 52 |
| SAP | 102 | 84 |
| MAP | 81 | 58 |
| EDP | 10.5 | 8.1 |
| dpdt | 2215 | 2000 |
| PTI | 24.5 | 19.4 |
| CENTRAL PP | 40 | 48 |
| Abd PP | 47 | 40 |
| Ao dpdt | 1420 | 1700 |

| PARAMETER (N=3) | % CHANGE BASELINE |
|---|---|
| HEART RATE | -15±3 |
| SYSTOLIC PRESSURE | -26.5±5 |
| LV DIASTOLIC PRESSURE | -41±3.3 |
| LV DIASTOLIC VOLUME | 1.2±0.5 |
| EJECTION FRACTION | 28±10 |
| STROKE VOLUME | 31±10 |
| CARDIAC OUTPUT | 12±6 |
| RESISTANCE | -40±7 |
| TAU | -15±5 |
| PEAK FILLING RATE | 14±6 |
| RPP | -25±4 |

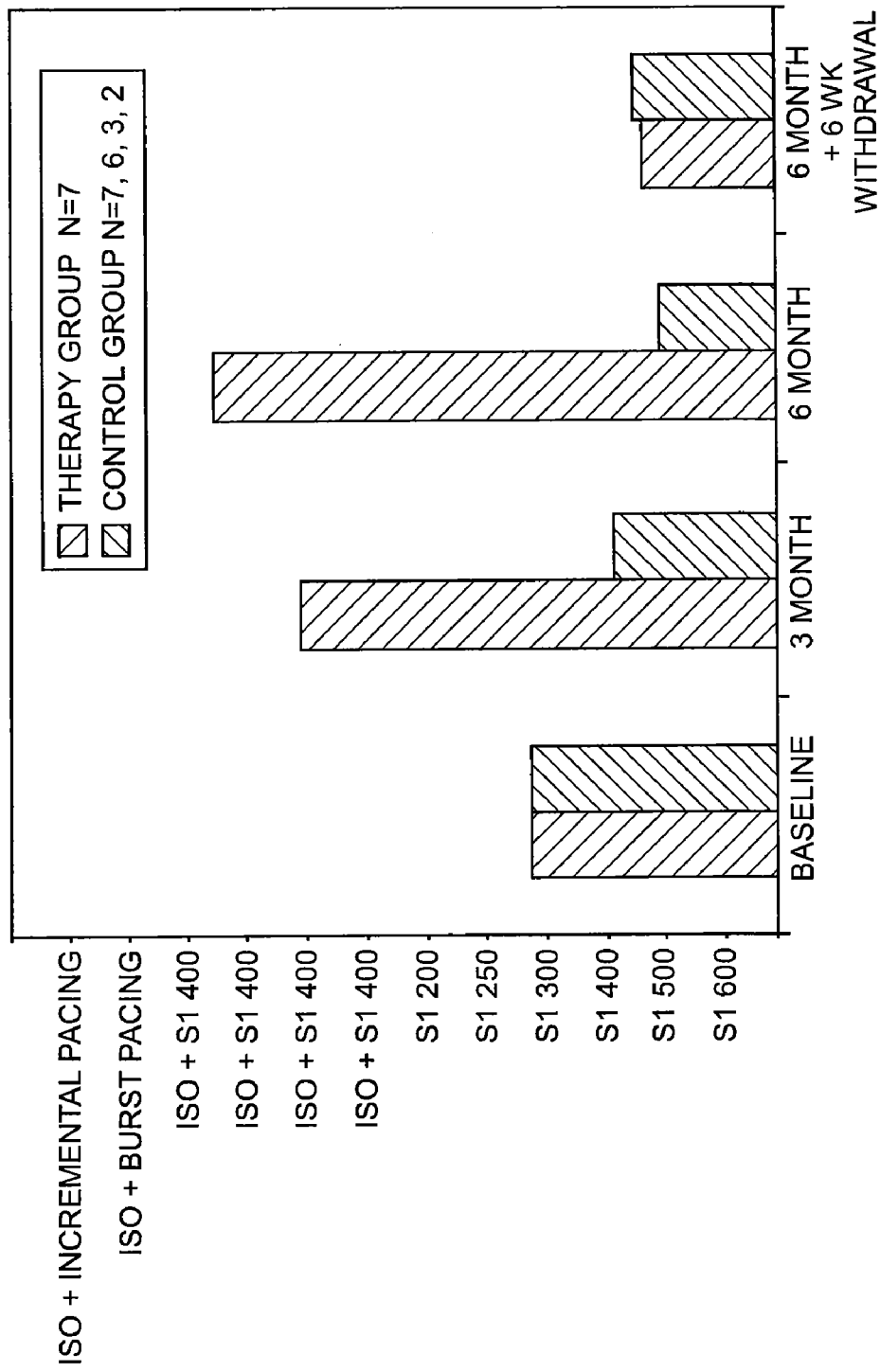

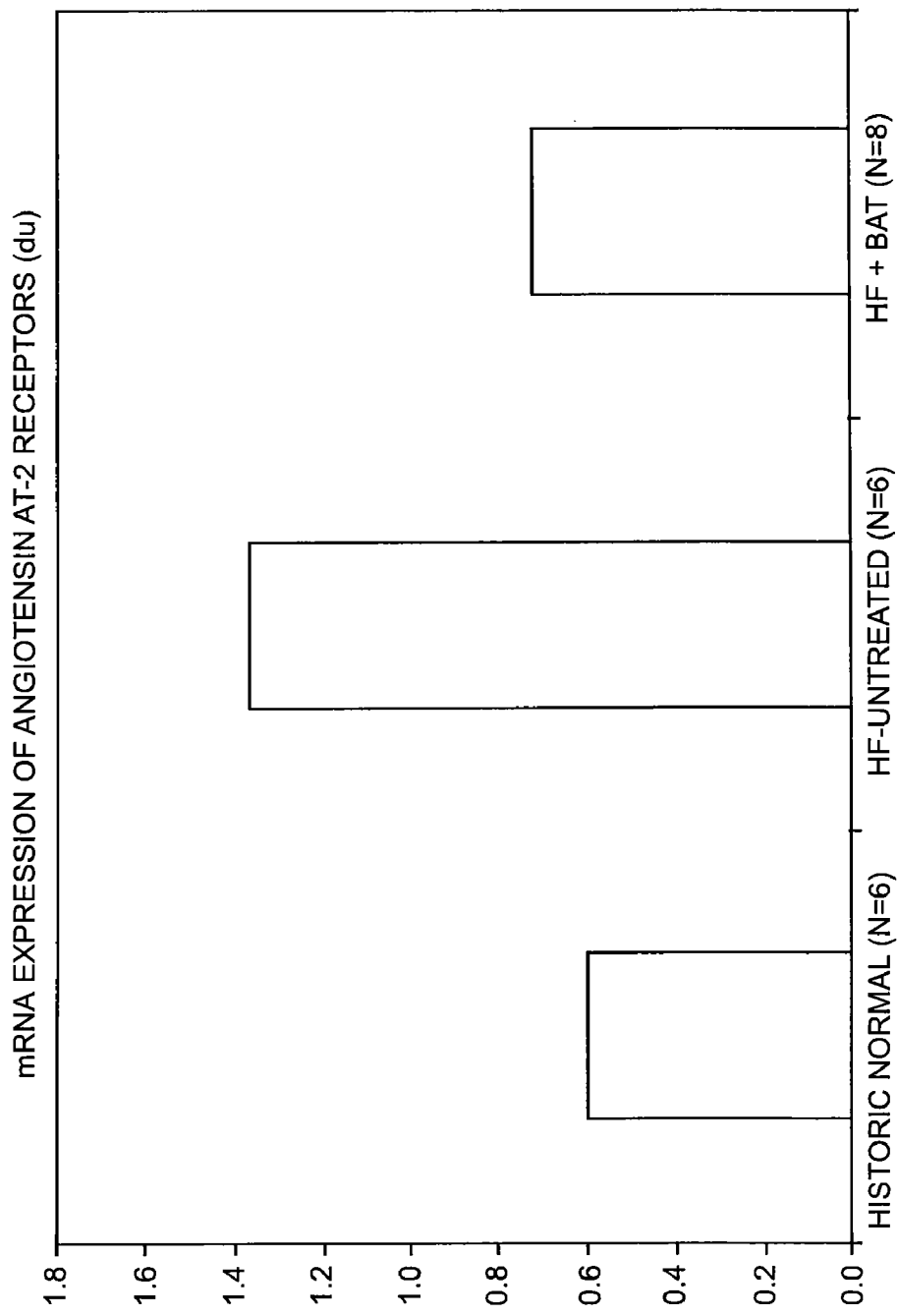

DEVICES AND METHODS FOR TREATMENT OF HEART FAILURE AND ASSOCIATED CONDITIONS

RELATED APPLICATIONS

This application is a divisional of U.S. patent application Ser. No. 12/485,895, filed Jun. 16, 2009, entitled "Device and Methods for Treatment of Heart Failure and Associated Conditions," which claims the benefit of U.S. Provisional Application No. 61/061,938, filed Jun. 16, 2008, entitled "Devices and Methods for Treatment of Heart Failure and Associated Conditions," the disclosures of which are hereby incorporated by reference in their entireties.

FIELD OF THE INVENTION

The present invention relates generally to medical devices and methods of use for the treatment and/or management of heart failure and associated conditions, and more specifically to devices and methods for controlling the baroreflex system for the treatment, diagnosis and/or management of heart failure and associated conditions and their underlying causes.

BACKGROUND OF THE INVENTION

Hypertension, or high blood pressure, is a major cardiovascular disorder that is estimated to affect over 50 million people in the United Sates alone, and is a leading cause of heart failure and stroke. It is the primary cause of death in over 42,000 patients per year and is listed as a primary or contributing cause of death in over 200,000 patients per year in the United States alone. Hypertension occurs in part when the body's smaller blood vessels (arterioles) constrict, causing an increase in blood pressure. Because the blood vessels constrict, the heart must work harder to maintain blood flow at the higher pressures. Sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke.

Sustained high blood pressure may eventually result in an enlarged and damaged heart (hypertrophy), which may lead to heart failure. Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state.

Heart failure can be generally classified into two categories: systolic and diastolic heart failure. The heart contracts and relaxes with each heartbeat—these phases are referred to as systole (the contraction phase) and diastole (the relaxation phase). Systolic heart failure (SHF) is characterized by low ejection fraction. In patients with diastolic heart failure (DHF), contraction may be normal but relaxation of the heart may be impaired. This impairment is generally caused by a stiffening of the ventricles. Such impairment is referred to as diastolic dysfunction and if severe enough to cause pulmonary congestion (increased pressure and fluid in the blood vessels of the lungs), diastolic heart failure. DHF patients differ from those patients with SHF, in that DHF patients may have a "normal" ejection fraction. However, because the ventricle doesn't relax normally, the pressure within the ventricle increases and the blood filling the ventricle exceeds what is "normal". People with certain types of cardiomyopathy may also have diastolic dysfunction.

Left ventricular hypertrophy refers to a thickening of the left ventricle as a result of increased left ventricular load. Left ventricular hypertrophy can be a significant marker for cardiovascular disorders and most common complications include arrhythmias, heart failure, ischemic heart disease, and sudden death. Although left ventricular hypertrophy (LVH) increases naturally with age, it is more common in people who have high blood pressure or have other heart problems. Because LVH usually develops in response to hypertension, current treatment and prevention mainly includes managing hypertension. Typical diagnosis involves the use of echocardiograms (ECHO) and electrocardiograms (ECG).

The SphygmoCor system (AtCor) provides a non-invasive assessment of the cardiovascular system and autonomic function. The SphygmoCor waveform provides physicians with clinically important information using a variety of cardiovascular parameters including augmentation index, augmentation pressure, central pulse pressure, central systolic pressure, and ejection duration. The SphygmoCor system comprises a non-invasive pressure transducer that uses a radial artery (external wrist) measurement and BP monitor. It works by using the pressure probe to record the pressure wave at the radial artery, which is then calibrated with the brachial blood pressure. However, this system does not provide a direct measurement of pressure, and the system is not able to be used as an implanted, continuous system.

Vascular stiffness in aging and its relation to cardiovascular disease is an important topic of current research. Vascular stiffness has been proposed as a risk factor for overall cardiovascular morbidity and mortality because of its suggested role in elevated blood pressure, increased left ventricular mass and heart failure. Current therapies targeting vascular stiffness, therefore, include those prescribed for these conditions, such as hypertension drug therapy. Pulse pressure is a known, simple measurement that can be used as a surrogate to aortic stiffness. Additionally, wave reflections can be inferred from detailed computer-aided pulse wave contour analysis, such as with the AtCor SphygmoCor system.

Heart failure is known to be a multi-organ disease and there is recent evidence that the gut (including the splanchnic circulation) plays an important role in cardiac diseases. The circulatory system of humans includes the pulmonary circulation and the systemic circulation. The pulmonary circulation ensures deoxygenated blood is returned to the lungs and oxygenated blood returned to the heart, while the systemic circulation ensures that oxygenated blood is supplied to the body. The systemic circulation includes the splanchnic circulation (or visceral circulation), which ensures that digestive organs receive blood through the vessels supplying the abdominal viscera. Acute decompensated heart failure or pulmonary congestion develops as a result of blood being redistributed from the splanchnic circulation to the pulmonary circulation, manifesting in fluid build-up in the chest and an inability of the patient to breathe. The specific mechanism of this transfer of fluids between the two is not yet fully understood.

The current standard of care for a patient exhibiting congestion is a variety of drugs, including diuretics, which causes excretion of fluid through the renal system. Splanchnic nerve stimulation has been described in the art to treat shock. For example, WO 2006/0031902 to Machado et. al teaches a method of treating hemodynamic derangement and controlling the mobilization of splanchnic circulation by stimulating the splanchnic nerve. Neither drug therapy, nor nerve stimulation therapy has been successful in providing a controlled therapy for congestive heart failure or acute decompensated heart failure.

A number of drug treatments have been proposed for the management of hypertension, heart failure, and other cardiovascular disorders. These include vasodilators to reduce the blood pressure and ease the workload of the heart, diuretics to reduce fluid overload, inhibitors and blocking agents of the body's neurohormonal responses, and other medicaments. Such medications can be effective for a short time, but cannot be used for extended periods because of side effects. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month.

Each of these approaches may be at least partly beneficial to patients, however, each of the therapies has its own disadvantages. For example, drug therapy is often incompletely effective. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease.

Accordingly, there continues to be a need for improved devices and methods for diagnosing, treating and/or managing high blood pressure, heart failure, and their associated cardiovascular and nervous system disorders.

SUMMARY OF THE INVENTION

Embodiments of the present invention, comprises devices and methods of use for the diagnosis, treatment and/or management of heart failure and associated conditions. In one embodiment, the present invention comprises devices and methods for controlling the baroreflex system of a patient for the treatment and/or management of heart failure and associated conditions and their underlying causes.

In one embodiment, the present invention comprises methods and devices of sensing, measuring, and monitoring parameters indicative of cardiovascular function. In one embodiment, an impedance sensor is provided on, in or proximate a blood vessel to obtain waveform data of blood movement in the vessel. The obtained waveform data provides information relating to a forward wave and a reflected wave of a heart beat and also to the augmentation index. In another embodiment, the obtained waveform may be used to calculate parameters indicative of cardiovascular disorders and associated conditions, such as splanchnic circulation or left ventricular mass. In a further embodiment, the sensed waveform may be used to provide feedback in conjunction with a delivered therapy, such as a baroreflex therapy or a cardiac resynchronization therapy.

Embodiments of the present invention recognize that real-time central pressure of a patient could provide diagnostic and clinically relevant information and that it would be advantageous to provide a means for obtaining direct, real-time central pressure waveform data and use such information for display in a clinical setting. It would additionally be advantageous to use such information in a closed-loop system to optimize therapies.

Embodiments of the present invention also recognize the advantages of being able to sense and monitor the movement of fluids between the splanchnic and pulmonary circulations and be able to use this information to titrate drug and other therapies. Embodiments of the present invention may also provide controlled therapy to modulate the fluid distribution in a patient, to treat congestion or prevent ensuing congestion.

Embodiments of the present invention also recognize the advantage of being able to measure and monitor vascular stiffness. Certain embodiments of the present invention provide a means for closed-loop monitoring of vascular stiffness in order to use such information to provide and optimize therapies to prevent and reduce vascular stiffness.

BRIEF DESCRIPTION OF THE DRAWINGS

The invention may be more completely understood in consideration of the following detailed description of various embodiments of the invention in connection with the accompanying drawings, in which:

FIG. 6 is a table of parameters that may be derived from the waveform of FIG. 5.

FIG. 6A illustrates additional information that can be derived from the central pressure waveform.

FIG. 7 is a chart depicting a reduction in augmentation index following application of a baroreflex therapy according to an embodiment of the present invention.

FIG. 8A is a table depicting patient physiological parameters following application of a baroreflex therapy according to an embodiment of the present invention.

FIG. 8B is a table depicting patient physiological parameters following application of a baroreflex therapy according to an embodiment of the present invention.

FIG. 8C is a table depicting patient physiological parameters following application of a baroreflex therapy according to an embodiment of the present invention.

FIG. 11 is a chart depicting patient physiological parameters following application of a baroreflex therapy according to an embodiment of the present invention.

FIG. 12 is a chart depicting levels of markers indicative of heart failure before and after application of a baroreflex therapy according to an embodiment of the present invention.

Figure 1B:
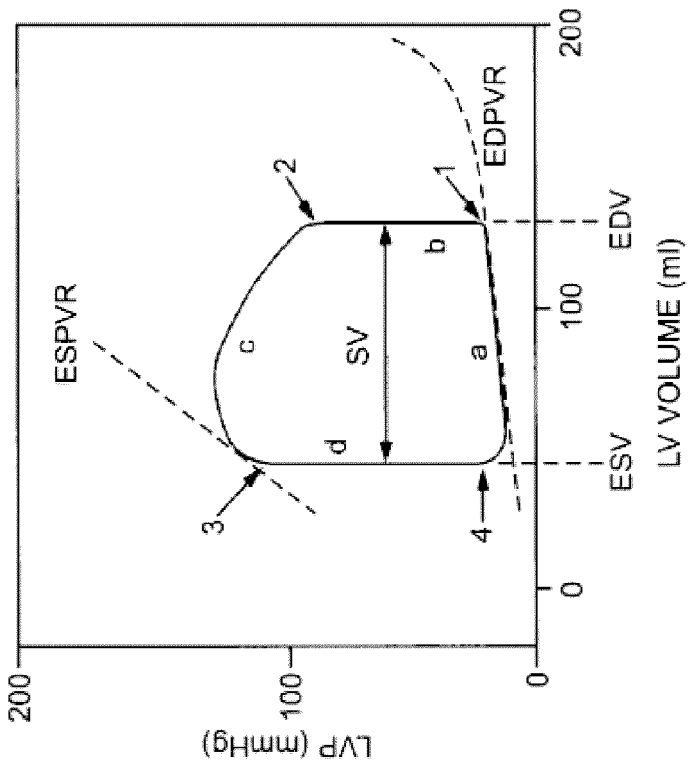
FIG. 1B is a graph of a PV loop.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Methods for treating heart failure and associated conditions in a subject typically comprise identifying a patient in need of treatment and stimulating a baroreflex with a baroreflex activation device to improve the symptoms and conditions associated with heart failure. In some variations, the baroreflex activation device is implanted proximate the baroreceptor, and in other variations, the baroreflex activation device is external. The stimulation provided by the baroreflex activation device may be any suitable stimulation. For example, it may be electrical stimulation, mechanical stimulation, thermal stimulation, chemical stimulation, or combinations thereof. In some variations the stimulation is electrical stimulation. The stimulation may be pulsed or continuous.

For additional information pertaining to cardiovascular anatomy and exemplary baroreceptor and baroreflex therapy systems, reference is made to the following patents and patent applications: U.S. Pat. No. 7,480,532 to Kieval et al., U.S. Pat. No. 7,480,271 to Kieval et al., U.S. Pat. No. 7,499,747 to Kieval et al., Published U.S. Patent Application No. 2006/0004417 to Rossing et al., Published U.S. Patent Application No. 2006/0074453 to Kieval et al., U.S. Pat. No. 7,835,797, to Rossing et al., U.S. Pat. No. 6,522,926 to Kieval et al., and U.S. Pat. No. 6,985,774 to Kieval et al., the disclosures of which are hereby incorporated by reference in their entireties.

In one embodiment, the invention provides a system and methods for obtaining a blood pressure waveform, and using the pressure waveform to derive parameters indicative of cardiovascular disorders. The waveform may be obtained independent of a therapy, such as for a stand-alone diagnostic and monitoring system, or the waveform may be used to provide feedback to a closed-loop therapy system. In such closed-loop system, one can use the waveform data to program, or adjust therapy to improve said cardiovascular disorders, and continuously monitor the status of the therapy in order to provide targeted, precise and controlled therapy.

The pressure waveform may be obtained with the use of electrodes positioned on, in or proximate a blood vessel, such as the carotid sinus or carotid artery. The electrodes measure impedance along or through the blood vessel. Methods and devices for obtaining blood vessel impedance measurements can be found in U.S. Pat. No. 8,116,873, filed Dec. 28, 2008, entitled "Measurement of Patient Physiological Parameters," the disclosure of which is incorporated by reference in its entirety. From the obtained impedance values, a waveform can be generated, such as in FIG. 5. The waveform may comprise a forward wave component and a reflected wave component. Suitable electrode arrangements for obtaining the waveform include an extravascular wrap having a plurality of electrodes positioned radially or longitudinally on the vessel, or an intravascular device resembling an electrophysiology catheter, having at least a plurality of electrodes. Signals from the sensor can be measured continuously or on an appropriate basis to gather hemodynamic information for the patient.

In one embodiment, the waveform data is used to determine the augmentation index, which is indicative of arterial stiffness. The system and methods of this embodiment increase venous reserve and capacitance, thereby improving vascular elasticity and vascular compliance with the majority of bodily vessels.

In one embodiment, the waveform data is indicative of LV mass and/or LV mass index. Referring to the waveform of FIG. 6A, the shaded area represents extra energy expenditure (Ew) imposed on the left ventricle during ejection. Referring still to FIG. 6A, Ew can be calculated as $2.09*(Ps-Pl)*(Ed-Tr)$, wherein Tr is the reflected wave time. This energy expenditure correlates with LV mass index, such that LV mass index can be monitored and logged with a waveform generated from an implanted transarterial impedance measurement device.

Well-known historical data on primary wave and augmentation index from a variety of sources demonstrated that reflected waves arrive earlier and central augmentation increases markedly with advancing age. Such data also supports speculation that central aortic stiffness and forward wave amplitude are the primary mechanism for increased central and peripheral systolic and pulse pressure with advancing age in healthy adults. It would be advantageous to reduce the amplitude of forward and reflected waves, as well as delay the reflected wave.

Figure 2:
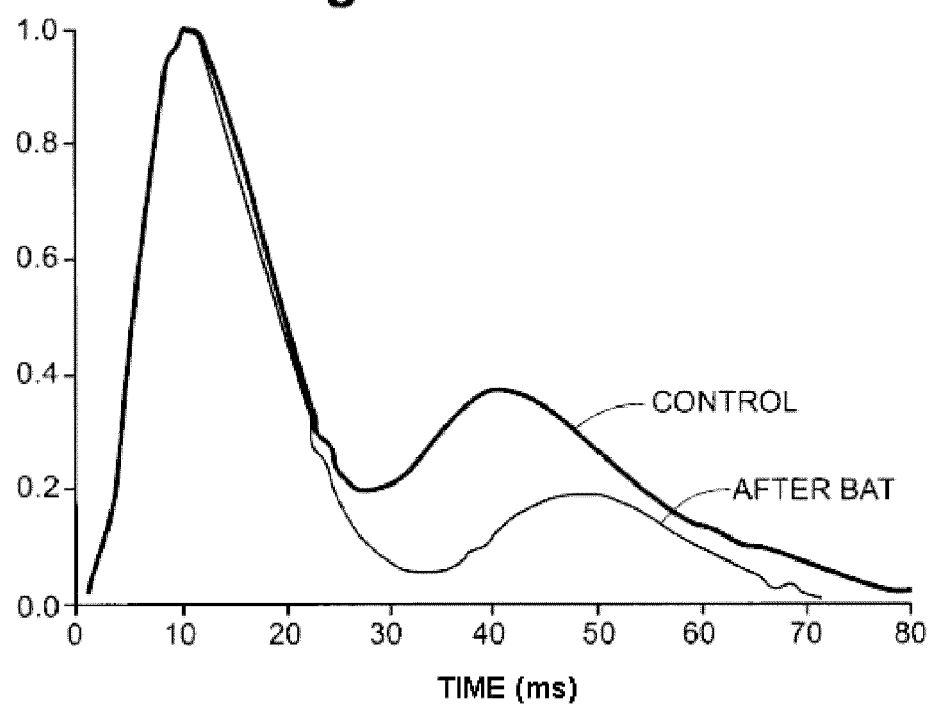
FIG. 2 is a graph depicting a reflected cardiac pressure wave before and after application of a baroreflex therapy to a canine according to an embodiment of the present invention.

To demonstrate the efficacy of the device and methods of the invention, experiments were performed on canines. FIG. 2 depicts the reduction in amplitude of the reflected wave as well as the delay in time of the reflected wave. This data suggests a significant improvement in the vascular properties after delivery of a baroreflex activation therapy (BAT).

Figure 3:
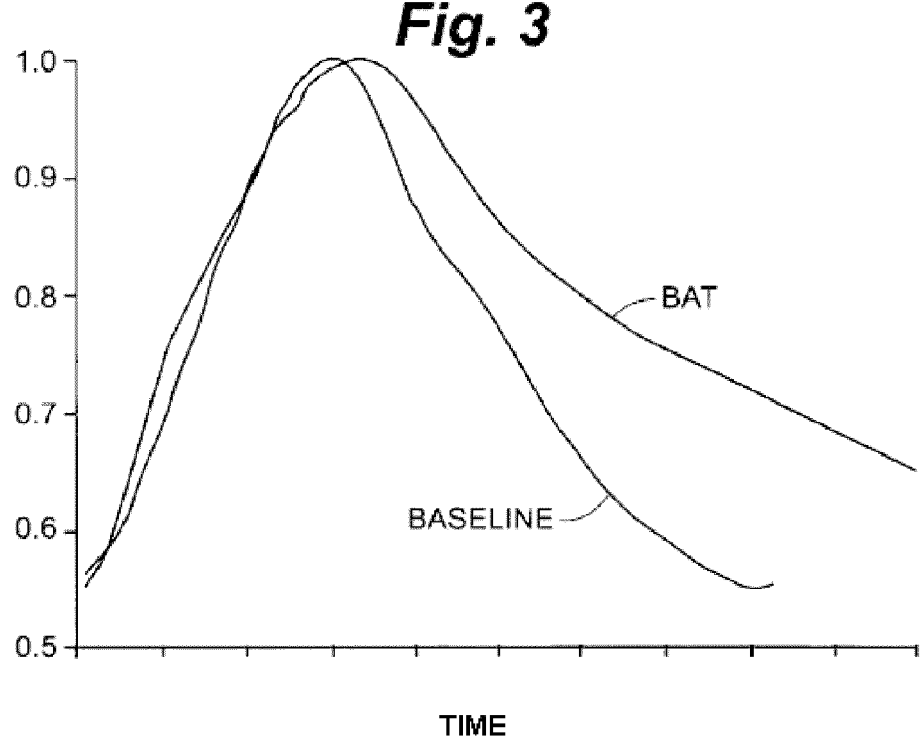
FIG. 3 is a graph depicting a reflected cardiac pressure wave before and after application of a baroreflex therapy to a human according to an embodiment of the present invention.

To demonstrate the efficacy of the present invention on human patients, studies were performed that measured the reflected wave before and after delivery of baroreflex activation therapy. FIG. 3 depicts the results illustrating the efficacy of baroreflex activation therapy in both reducing the amplitude of the reflected wave and delaying the time of the wave.

Figure 4:
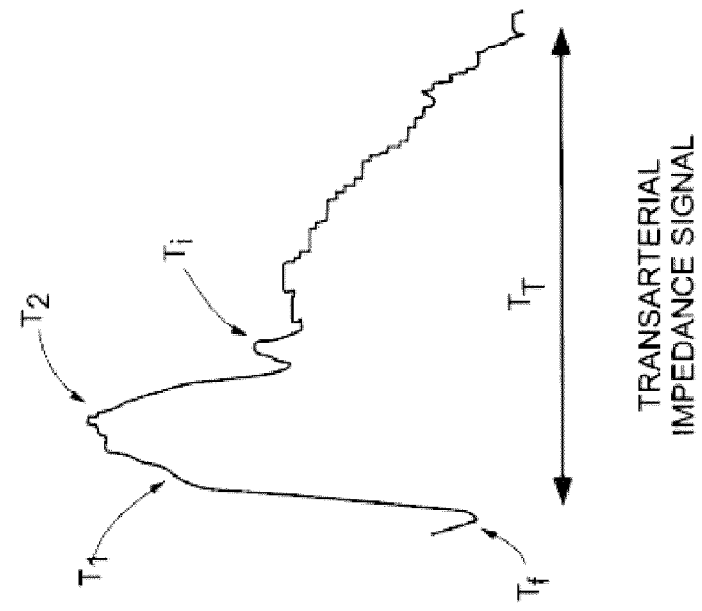
FIG. 4 is an example of a central pressure waveform.
Figure 5:
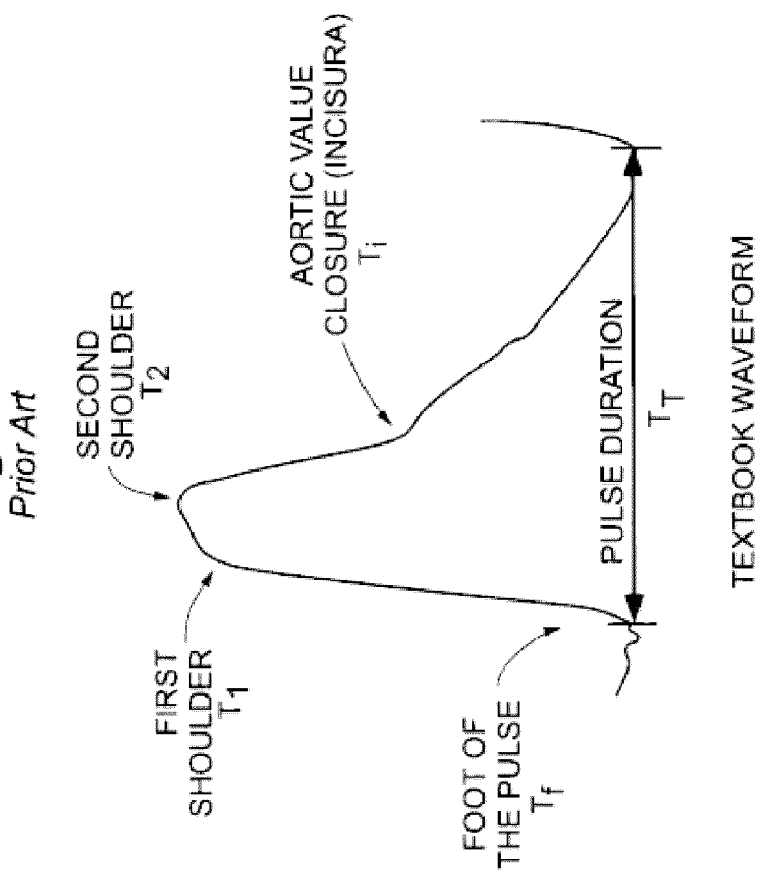
FIG. 5 is a central pressure waveform obtained by an embodiment of the present invention.

It is possible to derive many parameters from a pressure waveform. FIG. 4 depicts a "textbook" pressure waveform, while FIG. 5 depicts a pressure waveform obtained by a transarterial impedance measurement according to embodiments of the present invention. Reference numerals are used consistently throughout FIGS. 4-6A unless otherwise noted. Many parameters obtainable from the pressure waveform are presented in FIG. 6. While the derivation of these parameters from a pressure waveform has previously been known, until now it has not been possible to obtain such a waveform from a chronically-implanted arrangement, allowing real-time monitoring of a patient.

In one embodiment, the processed signal is displayable on a computer monitor so as to be readable by a physician. The physician may select one or more of the indices of interest. Such indices may include those, for example, in FIG. 6. In one embodiment, pulse wave velocity is derived. In one embodiment, the invention provides algorithms and computer-readable media to automatically generate the parameters of interest. In one embodiment, the invention may provide automated feedback to the therapy device in order to adjust or modify therapy based on these waveform-derived indices.

In one embodiment, the system derives augmentation index (AI) information and relies on the AI to adjust therapy. For example, if an AI is above a predetermined threshold level, baroreflex activation therapy is applied until the desired result (reduced AI) is achieved. In order to prove efficacy of baroreflex activation therapy in reducing AI in humans, an experiment was performed that delivered baroreflex activation therapy acutely to human implant patients. FIG. 7 depicts the results which conclude that AI was reduced when baroreflex activation therapy was delivered acutely in a human patient. Because AI is an indicator of arterial stiffness/compliance, this illustrates that baroreflex activation therapy affects arterial compliance, thereby reducing stiffness of vessels.

Benefits

Examination and analysis of pressure waveform data provides new insight to the effects of a baroreflex activation therapy. Embodiments of the invention have beneficial applications for diagnosing and managing heart failure and associated conditions. It has been observed experimentally that baroreflex activation therapy works by affecting a number of structures and function in the patient. Without limiting the scope of the invention, below is a list of observed benefits of the current invention and how each benefit may be measured or confirmed with the system of the invention.

One benefit is improved splanchnic circulation by way of increasing reservoir capacity of splanchnic circulation, resulting in net fluid transfer from lungs to gut. This fluid transfer may be measured by for example, trans thoracic impedance sensors that monitor fluid; other fluid sensors located for example in a vessel of the gut and a vessel of the pulmonary circulation; a sensor to measure elevated pulmonary artery pressure; monitoring weight gain; or monitoring incline during sleep.

Other benefits include reduced end diastolic pressure (EDP); increased cardiac output, measured by stroke volume and heart rate and by pulse contour methodology of the central pressure waveform; reduced diastolic stiffness, measured by −dp/dt, tau, edpvr; improved cardiac elasticity, measured by for example augmentation index; improved cardiac contractility, measured by arterial PV loop information derived from the central pressure waveform; +dp/dt, end systolic pressure-volume relationship (espvr); reduced likelihood that lone atrial fibrillation will occur; reduced likelihood that ventricular arrhythmias will occur; beneficial ventricular remodeling over time as evidenced by the changes in central pressure waveform; reduced detrimental remodeling that has previously occurred in the heart; reduced exercise intolerance as measured by patient activity with activity sensors; improved gut permeability; improved lung permeability; alleviation of fluid retention as measured by weight and other fluid sensors. Example embodiments of the present invention are described below.

Heart Failure

In one embodiment, sensors are used to monitor the fluids in a patient. Such sensors can be selected form a group consisting of edema sensors and other fluid/wetness sensors, chemical sensors, such as sensors to assay circulating plasma catecholamine, norepinephrine, angiotensin or BNP sensors, pressure sensors such as transarterial impedance, trans thoracic impedance, pulmonary artery or other intravascular pressure sensors and other pressure sensors. Such sensors can be located in a variety of locations including the heart, vessels, internal and external in order to measure parameters indicative of heart failure. Such sensors and methods of using them can be used as a stand alone system to monitor the build-up of fluids in the pulmonary circulation that is indicative of, for example heart failure. In another embodiment, such sensors can be used in a closed loop system with a therapy. In this embodiment, sensors monitor the presence or increase of fluids in the pulmonary circulation and provide baroreflex activation therapy. The sensors subsequently monitor the fluids in the splanchnic circulation and modulate therapy in order to move the fluids from pulmonary circulation to splanchnic circulation. Once the sensors sense the movement of fluids (that the pulmonary fluid has been reduced to an appropriate level), the therapy can be halted or adjusted to maintain the result. One could additionally use non-invasive methods to measure parameters conceived of by the inventions such as MRI and echocardiography.

In one embodiment, sensors are used to monitor the left ventricular mass of the patient in order to assess and monitor left ventricular hypertrophy. The methods of the invention could be used to treat patients exhibiting hypertrophy or as a monitor for ensuing hypertrophy in order to prevent it. Recent studies indicate that LVH was common at 1 year after heart transplantation, present in 83% of heart transplant recipients. Heart transplant recipients with severe LVH had significantly decreased survival. Therefore, the methods of the invention can be useful in the heart transplant population to monitor the development of hypertrophy and prevent it, thus improving outcomes for these patients. The sensors of the invention and methods of using them can be used as a stand alone system to monitor the LV mass, indicative of, for example left ventricular hypertrophy and heart failure or ensuing heart failure. In another embodiment, such sensors can be used in a closed loop system with a therapy. In this embodiment, sensors monitor the LV mass index in a patient and provide baroreflex activation therapy. The sensors subsequently monitor the LV mass and modulate therapy in order to reduce the LV mass. Once the sensors sense the reduction in LV mass, the therapy can be halted or adjusted to maintain the result.

To demonstrate efficacy of baroreflex activation therapy in human patients, experiments were performed to measure LV mass and related parameters. The experimental study results in FIGS. 8A and 8B using the LV Mass Index measurements and therapy methods of the invention show that baroreflex activation therapy reduced the following: blood pressure, LV wall thickness, LV mass, LV mass index (LVMI), and relative wall thickness.

Recent studies suggest that therapies which increase the diameter of the proximal aorta and left ventricular outflow tract (LVOT) may lower pulse pressure (PP) and thus may beneficially impact cardiovascular risk. As illustrated in FIG. 8B, baroreflex activation therapy increases LVOT diameter while reducing blood pressure, pulse pressure, and LVMI. Benefits are in addition to those achieved with intensive drug therapy.

In one embodiment, the present invention may reduce myocardial oxygen consumption (MVO2). MVO2 refers to the amount of oxygen consumed (or required) by the heart muscle for a contraction, and is increased under conditions such as in a heart failure patient, when heart rate is increased, contractility is increased, ventricular volume is increased, ventricular pressure is increased, etc. As described herein, heart failure is a cyclic mechanism where the body tries to compensate in response to reduced cardiac output. The increase in sympathetic tone results in increase in heart rate (to maintain cardiac output), an increase in peripheral arterial resistance (to maintain blood pressure), etc., and also an increase in MVO2 (to meet the myocardial oxygen demand). Thus, an increase in MVO2 means the heart is working much harder to meet the demand. Therefore, MVO2 is important in the assessment of heart failure, and therapy that reduces MVO2 would be useful in treating heart failure.

Baroreflex therapy works to reverse the sympathetic response and results in reduced MVO2 in patients as seen in FIG. 8C. Measuring the MVO2 indicates how hard the heart is working to contract and also whether the baroreflex therapy can be deactivated or reduced or whether it should continue or be increased until MVO2 falls within an accepted range (generally 7,000-10,000 bpm*mmHg in patients with systolic blood pressure of 120 mmHg and heart rate of 65-80 bpm). As can be seen in FIG. 8C, baroreflex therapy reduced MVO2 to acceptable levels within 4 months and continued to reduce it through 13 months.

In another embodiment, the present invention may improve arterial elasticity and/or vascular compliance. Arterial compliance is determined by structural factors, such as collagen and elastin, and functional factors, such as vasoactive neurohormones. The elastic behavior of conduit arteries contributes importantly to left ventricular function and aortic flow. Increased pulse pressure, an index of the pulsatile hemodynamic load, is a risk factor for the development of congestive heart failure. The increased pulsatile load that results from a decrease in arterial compliance reduces left ventricular stroke volume more so when the contractile state is depressed than in the normally functioning ventricle. Therefore, impaired arterial elasticity is particularly deleterious in patients with congestive heart failure.

Baroreflex therapy works to improve such factors as venous reserve and capacitance, thus improving elasticity of vessels. Measuring arterial compliance by means of such measures as augmentation index, and also pulse pressure (which is an indicator of aortic stiffness) can indicate a patient's propensity for or current heart failure status. FIG. 8C depicts measurements of arterial compliance with echocardiogram and is measured in units of mL/mmHg. The normal range for patients using this measurement is approximately 1-2 mL/mmHg depending on age (as compliance generally is reduced with age). As seen in FIG. 8C, baroreflex therapy results in increased arterial compliance at 4 months and continues to 13 months. Pulse pressure is also reduced.

Arterial PV Loops for Real-Time Measurement of Heart and Arterial Function

In one embodiment, the invention provides an implantable, real-time pressure-volume loop monitoring device. Pressure-volume loops and their relationships to various mechanisms of the heart have been described since the early 1900s. For example, Starling described the relationship between filling pressure of the ventricle and stroke volume in 1914. The well known Frank-Starling mechanism describes the ability of the heart to match an increased venous return with an augmented stroke volume. PV loops are currently used for measuring pressure and volume perioperatively.

Figure 1A:
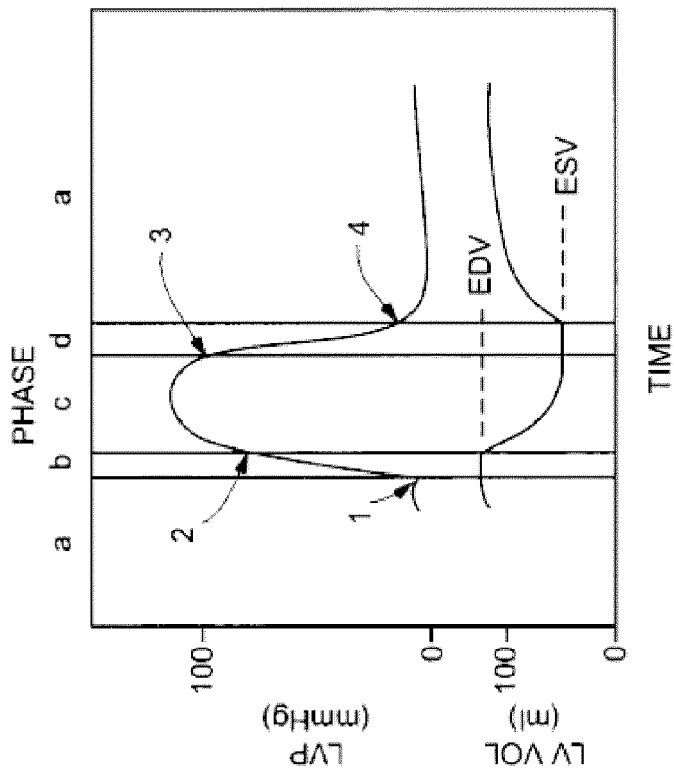
FIG. 1A is a graph of the cardiac phases.

Generally, left ventricular (LV) PV loops are derived from pressure and volume information found in a cardiac cycle diagram. To generate a PV loop for the left ventricle, the left ventricular pressure (LVP) is plotted against LV volume at multiple time points during a complete cardiac cycle. Various parameters related to cardiac function can be derived from LV loops. For example, parameters related to information such as ventricular filling, contraction, ejection, relaxation, end diastolic volume and end diastolic pressure can be obtained from PV loops and are known in the art. FIGS. 1A and 1B illustrate the cardiac phases and a typical PV loop, wherein 1 corresponds to the mitral valve closing, 2 corresponds to the aortic valve opening, 3 corresponds to the aortic valve closing, and 4 corresponds to the mitral valve opening. Further, a corresponds to diastolic filling, b corresponds to isovolumetric contraction, c corresponds to ejection, and d corresponds to isovolumetric relaxation.

In this embodiment, the left ventricular end-systolic pressure and stroke volume are measured and assessed continuously or as needed by a physician. In one embodiment, the system and methods of the invention provide a device that stimulates a baroreflex in order to reduce left ventricular pressure and increase left ventricular volume. In one embodiment, the device receives information from the PV loop monitor and adjusts therapy to optimize the result. In one embodiment, the pressure portion of the PV loop is derived from a transarterial pressure waveform. In one embodiment, the pressure portion is derived from an LV conductance catheter. In one embodiment, the pressure portion is derived from a pressure sensor in the aorta and the signal is obtained during the systole phase of the cardiac cycle. In one embodiment, the volume portion is derived from transarterial impedance waveform, which is derived from a flow measurement. In another embodiment, a separate sensor capable of determining blood flow is provided, and is used to generate the volume portion of the PV loop. In one embodiment reduced left ventricular pressure is confirmed by the implanted, real time, continuous PV loop of the invention. In one embodiment, the increased left ventricular volume is confirmed by the implanted, real time, continuous PV loop of the invention.

At least a portion of the PV loop can be generated from an impedance measurement on the aorta. During systole, the aortic valve is open, such that the pressure in the aorta the same as the pressure in the left ventricle. The impedance of the aorta is measured, and a pressure waveform is generated from the measured impedance values. In one embodiment, the pressure waveform may be processed to obtain a value indicative of flow, which can be integrated over time to obtain volume. From these values, the "top" portion of an LV loop (corresponding to systole) can be generated.

Figures 9A, 9B:
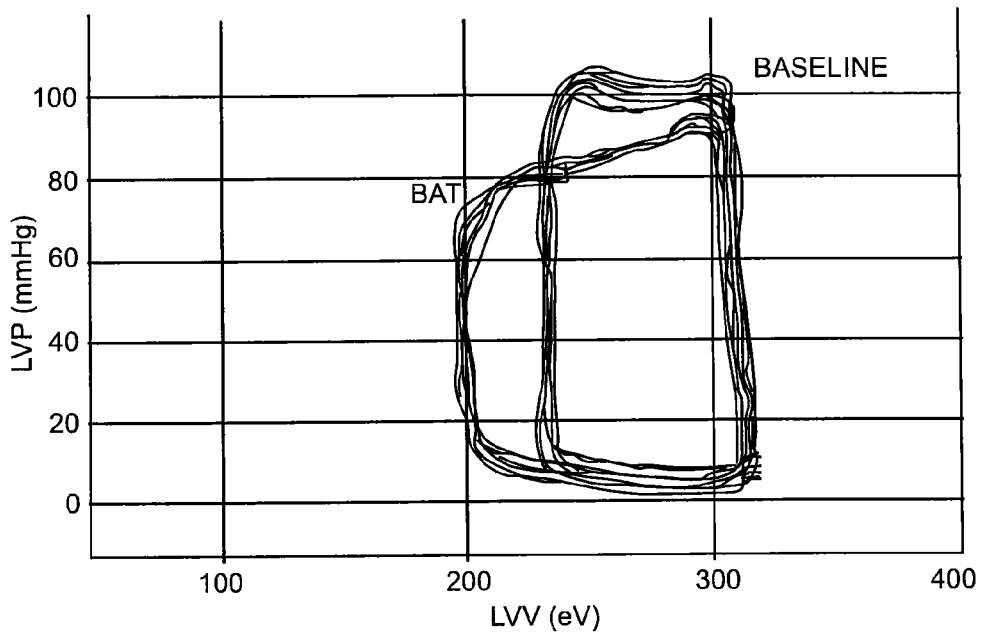
FIG. 9A is a graph depicting a PV loop before and after application of a baroreflex therapy according to an embodiment of the present invention.
FIG. 9B is a table depicting patient physiological parameters following application of a baroreflex therapy according to an embodiment of the present invention.
Figures 10A, 10B:
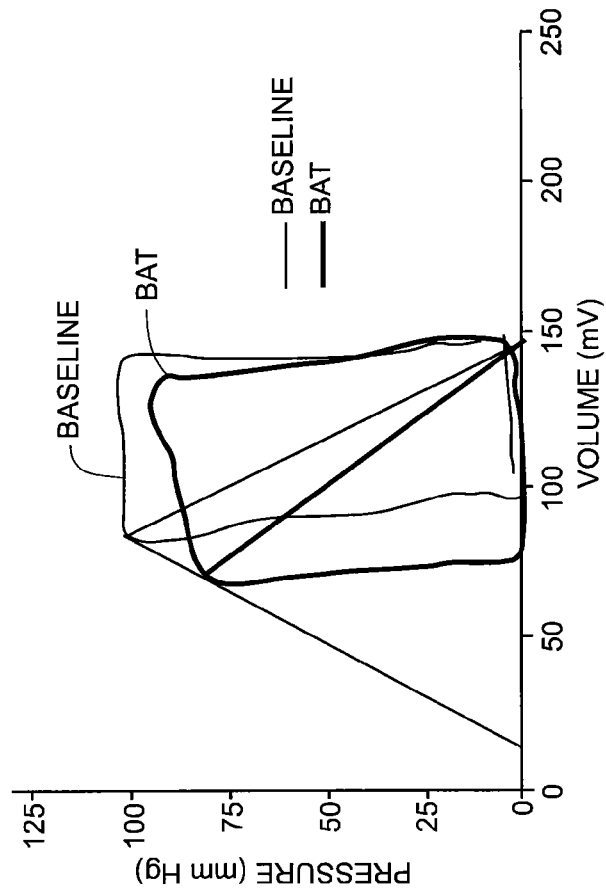
FIG. 10A is a graph depicting a PV loop before and after application of a baroreflex therapy according to an embodiment of the present invention.
FIG. 10B is a table depicting patient physiological parameters following application of a baroreflex therapy according to an embodiment of the present invention.

To demonstrate efficacy of baroreflex activation therapy effects on hemodynamic measures, experiments were performed on canines. FIGS. 9A-10B depict the reduction in LV pressure and increase in LV volume after BAT; FIG. 10B illustrates the hemodynamic characteristics. Referring specifically to FIG. 9A, the PV loop illustrates lower arterial pressures and increased stroke volumes following BAT. FIG. 9B illustrates that in a normal canine subject, application of baroreflex activation therapy reduces heart rate, reduces cardiac load (pressures), and slightly reduces the speed with which the heart contracts (dpdt). Reduced fatigue and improved coronary perfusion should occur in a patient that has received baroreflex activation therapy.

Referring to FIGS. 10A-10B, a reduction in heart rate and an increase in each of stroke volume, ejection fraction, and cardiac output can be seen following application of baroreflex activation therapy. Further, a reduction in Tau (time constant of LV relaxation) and an increase in peak filling rate indicate improved diastolic function. The rate-pressure-product (RPP) decrease indicates the heart is consuming less energy, despite the increased cardiac output.

Combined Baroreflex Therapy and Vagal Nerve Stimulation

In one embodiment, the invention comprises a system that improves the normalization of sympathetic/parasympathetic balance by combining baroreflex activation therapy with a vagal nerve electrode that provides efferent vagal nerve stimulation to the heart for more precise and robust heart rate control, or provides a stimulus to inhibit efferent vagal nerve activity to the heart if heart rate drops too low with baroreflex activation therapy. The advantages of this therapy for heart failure are that vagal nerve stimulation alone lowers heart rate but does not affect the vasculature. Current baroreflex activation therapy affects both heart rate and the vasculature but does not provide selective control of heart rate and blood pressure and may be perceived to cause precipitous drops in arterial pressure in certain heart failure patients. By providing an additional mechanism to augment the heart rate drop, this invention allows for greater heart rate and pressure control than either system alone.

The parasympathetic nervous system has a complementary relationship with the sympathetic nervous system. The body uses these two systems to regulate blood pressure. Stimulation or enhancement of the parasympathetic nervous system generally causes a decrease in blood pressure. Stimulating or enhancing the sympathetic nervous system, on the other hand, generally causes blood pressure to increase. If cardiac output is insufficient to meet demand (i.e., the heart is unable to pump sufficient blood), the brain activates a number of body systems, including the heart, kidneys, blood vessels, and other organs/tissues to correct this.

In one embodiment, baroreflex activation therapy is achieved by electrodes placed around the carotid sinus, and vagal nerve stimulation is achieved by an electrode placed around the right vagus nerve. In other embodiments, vagal nerve stimulation is achieved by an electrode placed intravascularly, for example, either in the jugular vein for stimulating the right vagus nerve, or in the superior vena cava to stimulate the cardiac branches of the vagus nerve. Using sensors for monitoring heart rate and blood pressure, the combined system alters baroreflex activation therapy intensity and vagal nerve stimulation intensity to achieve target heart rate reductions without compromising blood pressure. For example, if the heart rate target has not been achieved with baroreflex activation therapy, but the blood pressure target value has been achieved, vagal nerve stimulation is applied to reduce heart rate further.

The system is also programmable to alter intensities of baroreflex activation therapy and vagal nerve stimulation to achieve target blood pressures and heart rates in a more efficient manner than baroreflex activation therapy or vagal nerve stimulation alone. For example, when high intensity baroreflex activation therapy is required to achieve target heart rate but blood pressure is not too low, the system operates in a closed-loop fashion to reduce intensity of baroreflex activation therapy as much as possible, without losing any of the pressure response, while increasing vagal nerve stimulation to account for any loss of heart rate response. The system uses an algorithm to monitor blood pressure, heart rate, baroreflex activation therapy intensity, and vagal nerve stimulation intensity, to find the most efficient combination of baroreflex activation therapy and vagal nerve stimulation intensities to achieve target blood pressure and heart rate values. In the event that the baroreflex activation therapy intensity required for achieving a target pressure response causes heart rate to drop too far, the system inhibits efferent vagal nerve activity by providing vagal nerve stimulation to inhibit nerve traffic in the efferent direction, thereby counteracting the parasympathetic activity enhancement by baroreflex activation therapy.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature (including the pulmonary artery) and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

Arrhythmias

A study was performed examining the effects of baroreflex activation therapy on the induction of ventricular tachycardia or ventricular fibrillation in canines with intracoronary microembolization-induced advanced heart failure (LV ejection fraction ~20%). Canines with heart failure underwent programmed ventricular stimulation performed from the right ventricular apex. Stimulation parameters of the baroreflex therapy system were chosen for each subject in order to achieve a desired level of baroreflex activation therapy, measured as an approximate 10-20% drop in arterial pressure under anesthesia (1% isofluorane). Devices were then programmed to these stimulation parameters at the beginning of the therapy period and remained at these settings throughout the three month therapy period.

The results in FIG. 11 show that in addition to improving LV function and attenuating LV remodeling, long-term baroreflex activation therapy reduces the incidence of inducible lethal ventricular arrhythmias in canine patients with chronic advanced heart failure. This added benefit of baroreflex activation therapy provides further support for the use of this novel approach for the treatment of chronic heart failure.

CRT Therapy

In one embodiment, the pressure waveform is generated with information from a sensor located in for example an artery and used to input to a cardiac resynchronization therapy (CRT) device. In this embodiment, the CRT pulse is adjusted based on the measured time and/or amplitude variables obtained from the waveform. In one embodiment, the CRT programming adjustment can be made manually by for example a physician. In one embodiment, the pressure sensor is connected to the CRT therapy device and programming can be done automatically by the CRT device. In one embodiment, the device determines if the CRT therapy is working and adjusts the baroreflex activation therapy accordingly. For example, the device may use information for the derived pressure waveform and determine if the CRT is improving for example the reflected wave. If it is not, baroreflex activation therapy is applied until a desired reflected wave modification is seen.

Norepinephrine and Angiotensin II:

In one embodiment, a closed-loop system monitors circulating markers indicative of heart failure or ensuing heart failure. Possible markers could include but are not limited to norepinephrine, angiotensin II, aldosterone or BNP. Other known markers in the art could be used. In one embodiment, the HF marker monitoring system is used in combination with the baroreflex activation therapy system to monitor and adjust therapy in order to optimize efficacy and efficiency of the device.

Figure 13:
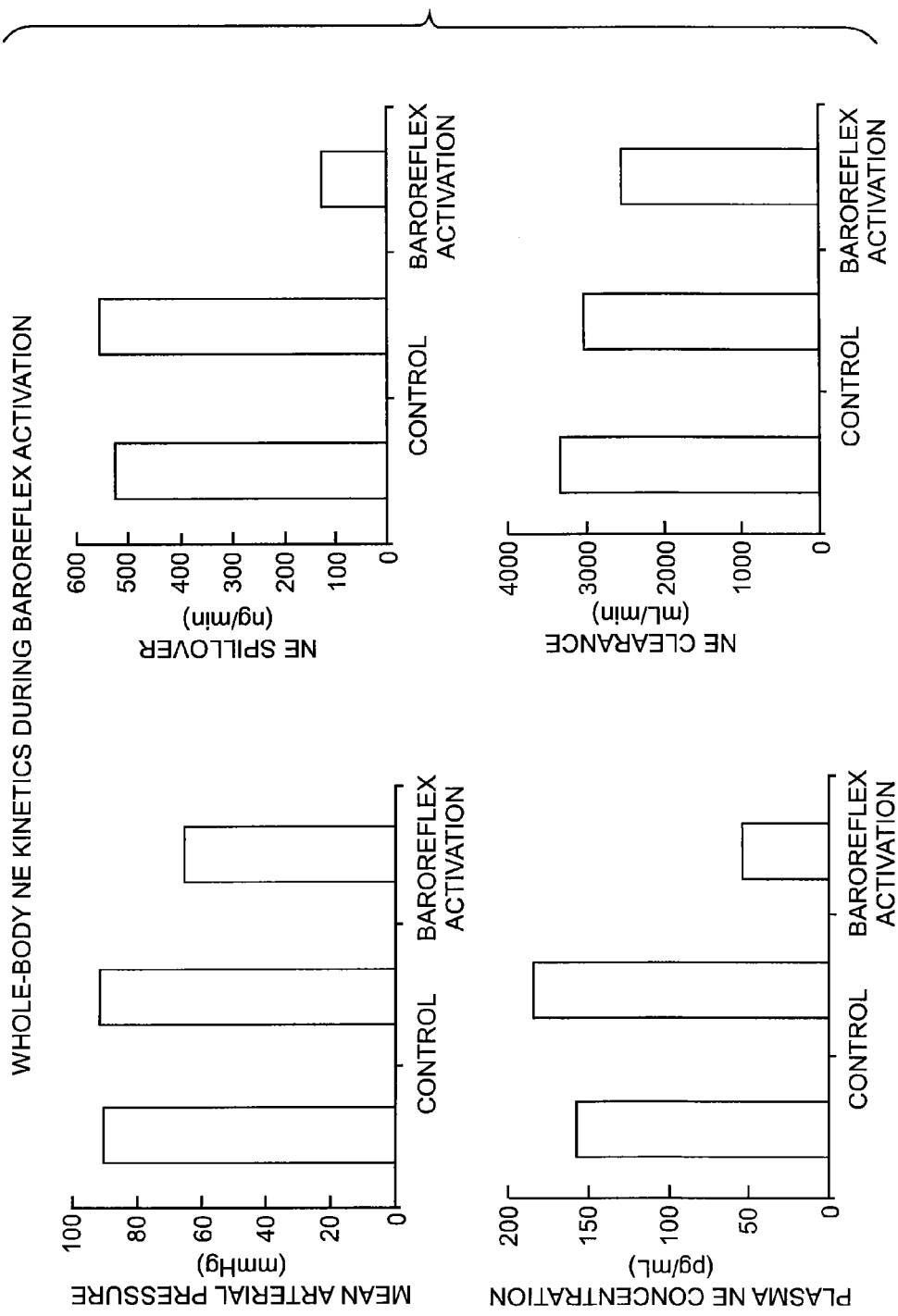
FIG. 13 is a group of charts depicting physiological parameters of control subjects compared to subjects that have received baroreflex therapy according to an embodiment of the present invention.

To prove efficacy of baroreflex activation therapy to reduce markers indicative of heart failure, studies were performed to measure norepinephrine (NE) and angiotensin II (ANG) plasma levels before and after baroreflex activation therapy in dogs with HF. Results indicate that baroreflex activation therapy of the carotid sinus delays the increase in plasma NE and ANG II and significantly enhances survival in dogs with pacing-induced HF. Chronic baroreflex activation therapy reduces renal vasoconstriction during exercise in dogs with pacing-induced HF. These data suggest that baroreflex activation therapy may be of benefit in the treatment of severe heart failure. FIGS. 12 and 13 depict the results of three separate experiments. FIG. 12 depicts mRNA expression of Angiotensin AT-2 Receptors (du) in dogs. FIG. 13 depicts the results of whole body NE kinetics during baroreflex activation therapy, including mean arterial pressure, plasma NE levels, NE spillover and NE clearance.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. A method, comprising:
   implanting a sensor within a patient;
   implanting a baroreflex therapy system within the patient, the baroreflex therapy system including an electrode;
   automatically detecting with the sensor an undesirable level of fluid in a pulmonary circulation of the patient; and
   automatically delivering a therapy with the baroreflex therapy system via the electrode in response to the detecting an undesirable level of fluid in the pulmonary circulation to reduce the level of fluid in the pulmonary circulation.

2. The method of claim 1, further comprising:
   upon detecting with the sensor an acceptable level of fluid in the pulmonary circulation, automatically delivering a second therapy with the baroreflex therapy system to maintain the acceptable level of fluid in the pulmonary circulation.

3. The method of claim 2, wherein automatically delivering the second therapy comprises cessation of therapy.

4. The method of claim 1, further comprising:
   implanting a second sensor within the patient:
   monitoring a level of fluid within a splanchnic circulation of the patient with the second sensor; and
   modulating the baroreflex therapy based at least in part on the level of fluid sensed within the splanchnic circulation.

5. A method, comprising:
   causing a baroreflex therapy system to be manufactured and made available to a user;
   causing a sensor to be manufactured and made available to the user; and
   providing instructions recorded on a tangible medium to the user, the instructions comprising:
   implanting the baroreflex activation device within a patient;
   implanting the sensor within the patient;
   causing the sensor to detect an undesirable level of fluid in a pulmonary circulation of the patient; and
   causing the baroreflex therapy system to deliver a therapy in response to the detecting an undesirable level of fluid in the pulmonary circulation, the therapy to reduce the level of fluid in the pulmonary circulation.

6. The method of claim 5, wherein the baroreflex therapy system includes an electrode, wherein the instructions for implanting the baroreflex therapy system within the patient further comprises implanting the baroreflex therapy system within the patient such that the electrode is proximate a baroreceptor, and wherein the instructions for causing the baroreflex therapy system to deliver a therapy further comprises causing the baroreflex therapy system to deliver a therapy to stimulate the baroreceptor via the electrode.

7. The method of claim 5, wherein the instructions further comprise:

implanting a second sensor within the patient;

monitoring a level of fluid within a splanchnic circulation of the patient with the second sensor; and causing the baroreflex therapy system to modulate the therapy based at least in part on the level of fluid sensed within the splanchnic circulation.

8. A therapy system, comprising:

an implantable baroreflex activation device including an electrode configured to be implanted proximate a baroreptor within a patient;

an implantable sensor configured to provide an indication of a fluid level within the patient;

a control system coupled to the baroreflex activation device and the sensor, the control system programmed to automatically:

detect a level of a fluid in a pulmonary circulation of the patient with the sensor; and upon detecting an undesirable level of the fluid in the pulmonary circulation, delivering a therapy via the electrode of the baroreflex activation device to reduce the level of fluid in the pulmonary circulation.

9. The system of claim 8, further comprising a second sensor operably coupled to the control system, wherein the first sensor and the second sensor are configured to provide transthoracic impedance.

10. The system of claim 8, further comprising a second sensor operably coupled to the control system, the second sensor configured to provide an indication of a fluid level within the splanchnic circulation of the patient to the control system, and wherein the control system is programmed to automatically modulate the therapy based at least in part on the indication of a fluid level within the splanchnic circulation of the patient.

11. The system of claim 10, further comprising a second sensor operably coupled to the control system, the second sensor configured to provide an indication of a posture of the patient to the control system, and wherein the control system is programmed to automatically modulate the therapy based at least in part on the indication of the posture of the patient.

12. The system of claim 8, further comprising a second sensor operably coupled to the control system, wherein the first sensor and the second sensor are implanted in contact with a blood vessel, and wherein the control system is configure to determine an impedance of the blood vessel using the first sensor and the second sensor.

\* \* \* \* \*